(12) United States Patent
Fischer et al.

(10) Patent No.: US 11,639,368 B2
(45) Date of Patent: May 2, 2023

(54) METHOD FOR PREVENTING AND TREATING HYPERPERMEABILITY

(71) Applicant: Apeptico Forschung UND Entwicklung GMBH, Vienna (AT)

(72) Inventors: Bernhard Fischer, Vienna (AT); Rudolf Lucas, Vienna (AT)

(73) Assignee: APEPTICO FORSCHUNG UND ENTWICKLUNG GMBH, Vienna (AT)

( * ) Notice: Subject to any disclaimer, the term of this patent is extended or adjusted under 35 U.S.C. 154(b) by 132 days.

(21) Appl. No.: 16/165,392

(22) Filed: Oct. 19, 2018

(65) Prior Publication Data
US 2019/0040105 A1 Feb. 7, 2019

Related U.S. Application Data

(63) Continuation of application No. 14/201,119, filed on Mar. 7, 2014, now abandoned, which is a continuation of application No. 13/254,273, filed as application No. PCT/AT2010/000056 on Mar. 5, 2010, now abandoned.

(30) Foreign Application Priority Data

Mar. 5, 2009 (AT) .................................. A 359/2009

(51) Int. Cl.
C07K 7/64 (2006.01)
A61K 38/12 (2006.01)
A61K 38/19 (2006.01)

(52) U.S. Cl.
CPC ................ *C07K 7/64* (2013.01); *A61K 38/12* (2013.01); *A61K 38/191* (2013.01)

(58) Field of Classification Search
None
See application file for complete search history.

(56) References Cited

U.S. PATENT DOCUMENTS

| 7,258,861 B2 * | 8/2007 | Lucas ....................... A61P 7/00 424/185.1 |
| 2003/0105021 A1 | 6/2003 | Lucas et al. |
| 2007/0154482 A1 | 7/2007 | Sukhatme et al. |
| 2011/0319316 A1 | 12/2011 | Fischer et al. |

FOREIGN PATENT DOCUMENTS

| DE | 60004340 T2 | 6/2004 |
| EP | 1264559 A1 | 12/2002 |
| EP | 2009023 A1 | 12/2008 |
| WO | 00/009149 A1 | 2/2000 |
| WO | 2005/087797 A1 | 9/2005 |
| WO | 2006013183 A1 | 2/2006 |
| WO | 2008/148545 A1 | 12/2008 |
| WO | WO-2008148545 A1 * | 12/2008 ........... C07K 14/525 |
| WO | 2009073909 A1 | 6/2009 |

OTHER PUBLICATIONS

Hamacher et al. "The lectin-like domain of tumor necrosis factor improves lung function after rat lung transplantation—potential role for a reduction in reactive oxygen species generation" Crit. Care Med. 38:871-878 (Year: 2010).*
Xiong et al. "The lectin-like domain of TNF protects from listeriolysin-induced hyperpermeability in human pulmonary microvascular endothelial cells—a crucial role for protein kinase C-alpha inhibition" Vascular Pharmacology 52:207-213. (Year: 2010).*
Shabbir et al. "Mechanism of Action of Novel Lung Edema Therapeutic AP301 by Activation of the Epithelial Sodium Channel" Mol. Pharmacol. 84:899-910. (Year: 2013).*
Shann F "Bacterial pneumonia: commoner than perceived" The Lancet 357:2070-2072 (Year: 2001).*
"American Lung Association ""Symptoms, Diagnosis and Treatment: Influenza"" http://www.lung.org/lungdisease/influenza/symptoms-diagnosis-treatment.html. Accessed Dec. 10, 2014. Published Apr. 7, 2013."
"American Lung Association ""Symptoms, Diagnosis and Treatment: RSV"" http://www.lung.org/lung-disease/respiratory-syncytialvirus/symptoms-diagnosis-treatment.html. Accessed Dec. 10, 2014. Published Feb. 23, 2012."
"American Lung Association ""Symptoms, Diagnosis and Treatment: SARS"" http://www.lung.org/lung-disease/severe-acuterespiratory-syndrome/symptoms-diagnosis-treatment.html. Accessed online Dec. 10, 2014. Published Apr. 19, 2012."
Bernard, G. R., et al., "Report of the American-European consensus conference on ARDS: definitions, mechanisms, relevant outcomes and clinical trial coordination," Intensive Care Med (1994) 20:225-232.
Berthiaume, Yves et al., "Alveolar edema fluid clearance and acute lung injury", Respiratory Physiology & Neurobiology 159 (2007) 350-359.
Groger, M., et al., "Peptide BB1-42 Preserves Endothelial Barrier Function in Shock," PloS One Apr. 2009 vol. 4 Issue 4 1-11.
Hamacher, J., et al., "The lectin-like domain of tumor necrosis factor improves ling function after rat lung transplantation—Potential role for a reduction in reactive oxygen species generation," Crit Care Med (2010) vol. 38., No. 3 871-878.
Hamacher, Jurg, Ternutaline Improves Ischemia-Reperfusion Injury After Left-Sided Rat Lung Translatation,: Experimental Lung Research (2009) 35:1-11.
Hazemi, P., et al., "Essential Structural Features of TNF-a Lectin-like Domain Derived Peptides for Activation of Amiloride-Sensitive Sodium Current in A549 Cells," J. Med. Chem. (2010) 53:8021-8029.

(Continued)

*Primary Examiner* — Sudhakar Katakam
*Assistant Examiner* — Zachary J Miknis
(74) *Attorney, Agent, or Firm* — Edwin S. Flores; Daniel J. Chalker; Chalker Flores, LLP

(57) ABSTRACT

A peptide is described, which consists of 7-17 adjacent amino acids and comprises the hexamer TXEXXE, wherein X, X and X can be any natural or non-natural amino acid, wherein the peptide has no TNF receptor binding activity and is cyclized, for the prevention and treatment of hyperpermeability of epithelial cells and endothelial cells.

14 Claims, 11 Drawing Sheets

Specification includes a Sequence Listing.

(56) References Cited

OTHER PUBLICATIONS

Lucas et al., Science, "Mapping the Lectin-Like Activity of Tumor Necrosis Factor" Feb. 11, 1994 vol. 263, pp. 814-817.
Lucas, Rudolf, et al., "Protein Kinase C-a and Arginase I Mediate Pneumolysin-Induced Oulminary Endothelial Hyperpermeability," Am. J. Resp Cell and Mole. Bio. (2012) vol. 47 1-9.
Mauad, Thais, et al., "Lung Pathology in Fatal Novel Human Influenza A (h1N1) Infection," Am J Respir Crit Care Med (2010) vol. 181 72-79.
Office Action [CA 2752890] dated Nov. 17, 2016.
RU 2001 140 057 English Translation of Office Action issued by Russian Patent Office dated Jan. 29, 2014.
Shabbir, Waheed et al. "Mechanism of Action of Novel Lung Edema Therapeutic AP301 by Activation of the Epithelial Sodium Channel" Mol Pharmacol 84:899-910, Dec. 2013.
Vadasz et al., "The lectin-like domain of tumor necrosis factor-a improves alveolar fluid balance in injured isolated rabbit lungs" Crit Care Med. May 2008 36(5), pp. 1543-1550.
VandenBroucke, Emily, et al., "Regulation of Endothelial Junctional Permeability," Ann. NY Acad. Sci. (2008) 1123 134-145.
Ware, Lorraine, et al., "The Acute Respiratory Distress Syndrome," New England Medical Journal May 4, 2000 1334-1349.
Wheeler, Arthur P., et al., "Acute lung injury and the acute respiratory distress syndrome: a clinical review," Lancet 2007 369 1553-1565.
Witzenrath, Martin, et al., "Role of pneumolysin for the development of acute lung injury in pneumococcal pneumonia," Crit Care Med (2006) vol. 34 No. 7 1947-1954.
Wyncoll, Duncan L.A., et al., "Acute respiratory distress syndrome," Lancet Aug. 7, 1999 354 497-501.
Xiong, Chenling et al. "The lectin-like domain of TNF protects from listeriolysin-induced hyperpermeability in human pulmonary microvascular endothelial cells—A crucial role for protein kinase C-a inhibition" Vascular Pharmacology 52 (2010) 207-213.

\* cited by examiner

Figure 8
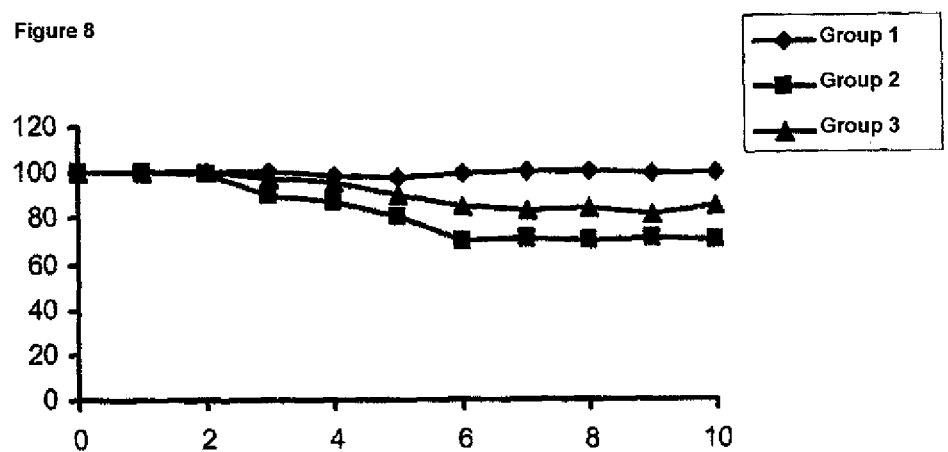
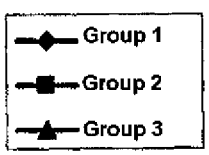
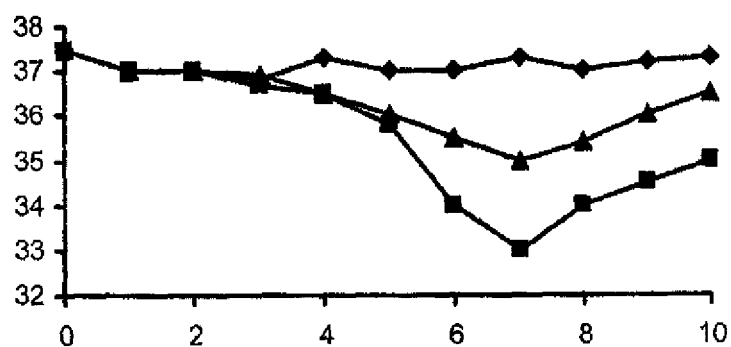
Figure 9
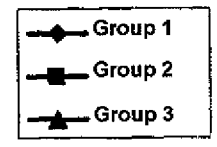
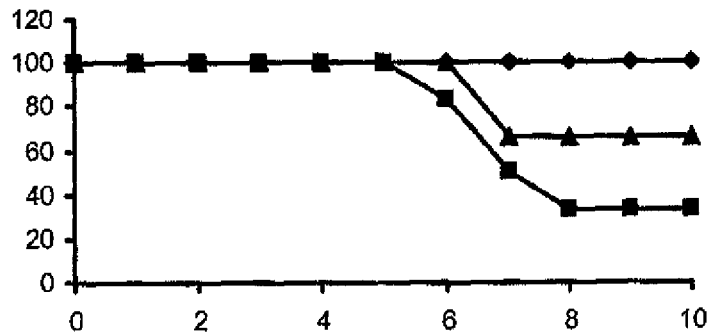
Figure 10

METHOD FOR PREVENTING AND TREATING HYPERPERMEABILITY

PRIORITY CLAIM AND CROSS-REFERENCE TO RELATED APPLICATIONS

The present application is a continuation application of U.S. patent application Ser. No. 14/201,119, filed Mar. 7, 2014, which is a continuation application of U.S. patent application Ser. No. 13/254,273, filed Sep. 1, 2011, which is a U.S. National Phase application of PCT Patent Application No. PCT/AT2010/000056, filed Mar. 5, 2010, which claims benefit of Austria Patent Application Serial No. A 359/2009, filed Mar. 5, 2009.

BACKGROUND OF THE INVENTION

The present invention relates to methods for preventing and treating hyperpermeability in endothelial cells and epithelial cells.

Endothelial cells and epithelial cells have decisive functions in all tissues and organs of the human and animal body.

The endothelium consists of a thin layer of endothelial cells. The layer of endothelial cells forms, among others, the inner surface of the blood vessels, like veins and capillaries, and the barrier between the blood and the outer wall of the blood vessels. Endothelial cells line the entire blood system, from the large blood vessels up to the smallest capillaries. Epithelial cells form single- or multi-layer cell layers, which cover all inner and outer body surfaces of the human and animal organs. Epithelial cells are in close proximity to each other and are rich in cell contacts. For epithelial cells, a distinction can be made into an outer, apical side facing towards the outside or the lumen, and a basal side. Furthermore, epithelial cells have an adhesion complex (junctional complex), consisting of zonula occludens (tight junction), zonula adhaerens (adhaerens junction) and desmosome (macula adhaerens), which on the one hand represents a physicochemical barrier and on the other hand interconnects adjacent epithelial cells.

For the physiological function of all animal and human organs and organelles, the intactness, in particular of the restricting cells and cell layers, is extremely important. If, for example, there is an injury of the endothelial cells or an injury of the endothelium of the blood vessels, respectively, liquid can escape from the blood vessels and result in massive disturbances in the vitality of the entire organism.

If, for example, there is an injury of the epithelial cells or an injury of the epithelium of organs, liquid can escape from the organs or liquid can penetrate, respectively, and thus seriously damage the functionality of the organs.

An injury of the endothelium and the epithelium may cause a so-called hyperpermeability, i.e. an uncontrolled passage of liquid from blood vessels into vital organs and tissues.

Beside mechanical causes, an infection or the impact of toxins can result in hyperpermeability. Microbial toxins are pore-forming molecules binding to cholesterol, which are released by gram-positive bacteria. Due to the effect of toxins, first pores are formed in cell membranes, and then macro-pores. Thus, cell layers become permeable for liquid and substances contained therein.

Known toxins are, among others, listeriolysin from *Listeria monocytogenes* or also pneumolysin from *Streptococcus pneumoniae*. These toxins can result in the formation of reactive oxygen molecules in the cells. The reactive oxygen molecules caused by toxins then result in damages to endothelium and epithelium due to the fact, among others, that the barrier function of the cells is damaged.

For retention of the barrier function of endothelial cell layers and epithelial cell layers, the cells are interconnected via protein fibers. Components of such protein fibers are e.g. the myosin light chain. However, due to phosphorylation of the myosin light chain, stresses are caused in the cells and the cell-cell connections, and intercellular gaps are formed, whereby liquid can penetrate and also leak in an uncontrolled manner.

A further component in the regulation of the barrier function of the epithelial cells and endothelial cells is protein kinase C. For protein kinases C, several isoenzymes are known, e.g. protein kinase alpha and zeta. These protein kinase C isoenzymes are activated by reactive oxygen molecules, hydrogen peroxide, microbial toxins, like pneumolysin and listeriolysin, and hydrophilic coronavirus proteins. Activated protein kinase C additionally results in a reduction of the expression of the epithelial sodium channel (ENaC), which is responsible for the sodium and liquid transport in epithelial cells, and thus, activated protein kinase C essentially contributes to the development of hyperpermeability.

Further causes for the development of hyperpermeability in the lungs are e.g. viruses, like influenza viruses, the severe acute respiratory syndrome-associated coronavirus (SARS-CoV) or the respiratory syncytial virus, which can result in hyperpermeability of the endothelium and epithelium as well as in atypical pneumonia. It is known that SARS-CoV proteins due to the activation of the protein kinase C isoform result in a reduction of the size and activity of the epithelial sodium channel, which promotes the development of hyperpermeability. It is also known that for these viral diseases of the lungs, the frequently used beta-2 adrenergic agonists show no effect.

Thus, in total, it is known that microbial toxins result in an increased level of reactive oxygen molecules in endothelial and epithelial cells. This causes phosphorylation of the myosin light chain, which again results in a disturbance of the cell-cell interaction and in the development of hyperpermeability.

Microbial toxins, reactive oxygen molecules as well as viral proteins result in an activation of protein kinase C isoenzymes. The activation of protein kinase C then results in a decrease of the expression of the epithelial sodium channel (ENaC) and the inhibition of its activity. These mechanisms, too, result in the development of hyperpermeability in the endothelium and epithelium.

Hyperpermeability of lung tissues is an essential component of various diseases of the lungs, e.g. acute lung injury, acute respiratory distress syndrome (ARDS), pneumonia. Currently, there is no standard therapy for treating hyperpermeability of the endothelium and epithelium.

US 2003/0185791 A1, EP 2 009 023 A1, WO 2006/013183 A1, EP 1 264 559 A1 and Marquardt et al. (J. Pept. Sci. 13 (2007): 803-810) disclose TNF-derived peptides for treating edemas.

SUMMARY OF THE INVENTION

The object of the present invention therefore is to provide means and methods, by means of which diseases, for which the prevention of hyperpermeability of epithelial cells and endothelial cells plays an essential role in the treatment, in particular lung diseases, like acute lung injuries, ARDS or viral lung diseases, can be prevented or treated.

In particular, the invention is to provide a biologically effective molecule for the prevention and treatment of hyperpermeability of the endothelium and epithelium and for the prevention and treatment of acute lung damage and the consequences of pneumonia.

Accordingly, the present invention relates to a peptide, which consists of 7-17 adjacent amino acids and comprises the hexamer TXEXXE (SEQ ID No. 13), wherein X, X and X can be any natural or non-natural amino acid, wherein the peptide has no TNF receptor binding activity and is cyclized, for the prevention and treatment of hyperpermeability of epithelial cells and endothelial cells.

Preferably, the present invention relates to a peptide consisting of 7-17 adjacent amino acids and comprising the hexamer TPEGAE (SEQ ID No. 4), wherein the peptide has no TNF receptor binding activity and is cyclized, for the prevention and treatment of hyperpermeability of epithelial cells and endothelial cells.

One particularly preferred embodiment of the present invention relates to a cyclized peptide consisting of a sequence of consecutive amino acids selected from the group consisting of QRETPEGAEAKPWY (SEQ ID No. 5)

PKDTPEGAELKPWY (SEQ ID No. 6)

CGQRETPEGAEAKPWYC (SEQ ID No. 1)
and

CGPKDTPEGAELKPWYC (SEQ ID No. 7)

and fragments of at least 7 amino acids thereof, which fragments include the hexamer TPEGAE (SEQ ID No. 4), for manufacturing of a drug for preventing and treating hyperpermeability of epithelial cells and endothelial cells.

The peptides according to the invention are preferably used for preventing the outbreak of or for treating pneumonia, acute lung injury, acute respiratory distress syndrome (ARDS) or bacterial or viral lung diseases, in particular infections with *Listeria monocytogenes*, *Streptococcus pneumoniae*, influenza viruses, SARS or RSV. The cause of pneumonia, which can be treated or prevented according to the invention, is independent of the cause of pneumonia and independent of whether it is an acute or chronic inflammation. Accordingly, according to the invention, preferably pneumonias, which are caused by an infection with bacteria, viruses, mycoplasmas, protozoa, worms or fungi, can be treated, but also toxically (e.g. by inhalation of toxic substances) or immunologically caused pneumonias or such ones caused by radiation (e.g. X-Rays, radiation therapy in cancer patients). Especially for pneumonias caused by inhalation of toxic substances or radiation, the preventive aspect of the present invention is particularly essential, however, also for bedridden persons, in particular older people, or for immunocompromised persons, like HIV patients or transplant patients. In particular, according to the invention, the pneumonia can be fought or prevented at a time, when no damages are recognizable on the X-ray yet.

Pathogens of primary pneumonias are mostly pneumococci, staphylococci, *Haemophilus influenzae*, mycoplasmas, chlamydia, legionella (*Legionella pneumophila*) and viruses like the flu virus, adenovirus and parainfluenza viruses. For secondary pneumonias, the spectrum of pathogens is shifted to Herpes viruses (CMV, HSV), fungi, *Pneumocystis jirovecii*, protozoa (toxoplasmosis) as well as anaerobic bacteria. In particular pneumonias caused by these pathogens are, according to the invention, particularly preferably treatable or (in particular in respect of secondary pneumonias) preventable, respectively.

The peptides according to the invention are for example known from the European patent EP 1 264 599 B1 and were suggested in the state of the art for the treatment of liquid accumulations (lung edema) and in particular for the re-absorption of these liquid accumulations, wherein the edema liquid is returned from the alveoli of the lung tissue into the capillaries, i.e. pumped out of the alveoli.

According to the invention, it was completely surprisingly demonstrated, that these peptides also influence the opposite liquid flow via the endothelium of the capillaries into the epithelium of the lung, however, in a contrary manner: while for the treatment of edemas, the transporting out of the liquid requires open and fully active pumping mechanisms, according to the invention, the passage of the liquid into the alveoli is stopped; the influx is thus prevented in the first place. The activation of edema resorption according to EP 1 264 599 B1 by the peptides according to the invention therefore seems to be based on a completely different mechanism—running in the opposite direction and in a regulating manner—than the reduction of hyperpermeability according to the invention, based on injuries of the endothelium and epithelium layers, whereby edemas are even prevented by avoiding the liquid transfer into the alveoli. Accordingly, with the present invention, completely new and surprising indications open up for the peptides according to the invention—beside the edema treatment from EP 1 264 599 B1 (which is only indicated at a later stage of the course of the disease).

Accordingly, the present invention is based on the circumstance, which was also found within the course of the work for the invention, that the peptides used according to the invention, as defined in EP 1 264 599 B1, influence the effects of toxins, reactive oxygen molecules, the activation of protein kinase C, the phosphorylation of the myosin light chain, and the expression of the epithelial sodium channel. This was not to be expected based on the existing knowledge about these peptides.

A very particularly preferred peptide according to the present invention consists of the amino acid sequence CGQRETPEGAEAKPWYC (SEQ ID No. 1) and is cyclized via the C residues (at positions 1 and 17).

The cyclization of the peptides according to the invention may either be achieved via a direct cyclization with a disulfide bridge between the two C residues at the N and C terminus or by coupling the peptide via both cysteines to a carrier substance. In that, in the peptides according to the invention, the cysteine residues are preferably provided at the beginning and at the end of the molecule. Other functional groups achieving a cyclization of the peptide can also be used, e.g. with an acid group resulting in an amide or ester ring closure with an amine or alcohol (for that, e.g. the amino acids aspartic acid and glutamic acid can be preferably intramolecularly cyclized with serine, threonine, tyrosine, asparagine, glutamine, or lysine). Therefore, further preferred peptides according to the invention are, for example, CGQKETPEGAEAKPWYC (SEQ ID No. 8), CGQRETPEGAEARPWYC (SEQ ID No. 9), CGQRETPEGAEAKPC (SEQ ID No. 10), CQRETPEGAEAKPWYC (SEQ ID No. 11), or CGQRETPEGAEAKFWYC (SEQ ID No. 12).

As carrier substances, any common pharmaceutically acceptable substances can be used, which are able, e.g., to form a covalent bond with the SH groups of the cysteines, wherein common carrier proteins, like keyhole limpet hemocyanin (KLH), tetanus toxin, etc. are particularly suited. Adjacent bifunctional residues may also be provided at the carrier (e.g. acid group beside amine or alcohol group). In this connection, it is important that "cyclization" comprises the intramolecular ring closure as well as the integration of a carrier (from which the bound peptide protrudes (with the N and the C terminus of the peptide being bound to the carrier)), wherein the peptide cyclized in such manner shows the cyclic three-dimensional structure and is respectively stabilized.

The peptides according to the invention may preferably be used for protecting epithelial cells and endothelial cells against hyperpermeability caused by reactive oxygen molecules or by bacterial toxins.

The peptides according to the invention may also be used for inhibiting the phosphorylation of the myosin light chain, for inhibiting the activation of protein kinase C or for increasing the expression of the epithelial sodium channel.

In that, the peptides according to the invention can be used for treating hyperpermeability caused by reactive oxygen molecules, microbial toxins, gram-positive microorganisms or pulmonary virus infections.

According to a further aspect, the present invention relates to a pharmaceutical composition containing a peptide according to the invention (or a mixture of various peptides according to the invention) and a pharmaceutical carrier. According to the invention, this pharmaceutical composition is used for preventing and treating hyperpermeability, as described above, in particular for preventing and treating pneumonia, acute lung injury, acute respiratory distress syndrome (ARDS) or viral lung diseases, in particular infections with *Listeria monocytogenes, Streptococcus pneumoniae*, SARS, RSV or influenza viruses, in particular influenza A viruses. The term "a pharmaceutical composition" refers to any composition comprising a peptide as defined above, which prevents, enhances or heals the conditions described herein. In particular, the term "a pharmaceutical composition" refers to a composition having a peptide as described above and a pharmaceutically acceptable carrier or excipient (both terms may be used interchangeably). Suitable carriers or excipients known to the expert are saline solution, Ringer's solution, dextrose solution, Hank's solution, fixed oils, ethyl oleate, 5% dextrose in saline solution, substances improving isotonia and chemical stability, buffers and preservative agents. Further suitable carriers include any carrier, which does not induce the production of antibodies itself, which are harmful for the individual receiving the composition, like proteins, polysaccharides, polylactic acids, polyglycolic acids, polymeric amino acids and amino acid copolymers. In that, the peptide according to the invention may also be cyclized to these carriers via a direct covalent bond. This pharmaceutical composition may (as a drug) be administered using any suitable method known by the expert. The preferred administration path is parenteral, in particular by inhalation (with aerosols) or intravenous administration. For parenteral administration, the drug of this invention is formulated in an injectable unit dosage form, like a solution, suspension or emulsion, in connection with the pharmaceutically acceptable excipient defined above. Dosage and type of administration, however, depend on the individual. In general, the drug is administered such that the peptide of the present invention is administered at a dose of between 1 µg/kg and 10 µg/kg, more preferably between 10 µg/kg and 5 mg/kg, most preferably between 0.1 and 2 mg/kg. Preferably, it is administered as a bolus dose. A continuous infusion may be used as well. In this case, the drug may be infused at a dose of between 5 and 20 µg/kg/minute, more preferably between 7 and 15 µg/kg/minute.

According to the present invention, a particularly preferred peptide according to the invention has the following amino acid sequence: SEQ ID No. 1 (NH2)Cys-Gly-Gln-Arg-Glu-Thr-Pro-Glu-Gly-AlaGlu-Ala-Lys-Pro-Trp-Tyr-Cys(COOH).

The determination of the concentration of reactive oxygen molecules in cultivated endothelial cells of the lungs showed that upon culture of the endothelial cells under a normal oxygen content of 21% (normoxic gas mixture), there is only a low formation of reactive oxygen molecules. With lack of oxygen (0.1% of oxygen, hypoxic gas mixture), however, there is a 3-fold increased formation of reactive oxygen molecules. If, however, a peptide according to the invention, in particular peptide SEQ ID No. 1, is added to endothelial cells cultivated under lack of oxygen (oxygen content 0.1%, hypoxic gas mixture), surprisingly no reactive oxygen molecules are formed by the endothelial cells.

Further examinations determined the electric resistance of cell layers of human endothelial and epithelial cells by means of electrical cell-substrate impedance analysis before, during and after the addition of the microbial toxins pneumolysin and listeriolysin. The examinations showed, that with an addition of 125 ng/ml and 250 ng/ml of listeriolysin to cultivated human endothelial cells, the development of hyperpermeability is initiated. This process was still enhanced by a toxin concentration of 250 ng/ml of listeriolysin. The addition of 62.5 ng/ml of pneumolysin to cultivated human endothelial cells also resulted in the development of hyperpermeability. This process was still enhanced by a toxin concentration of 125 ng/ml of pneumolysin. Surprisingly, however, it was found, that with the addition of a peptide according to the invention, in particular 50 µg/ml of peptide SEQ ID No. 1, the pneumolysin-induced as well as the listeriolysin-induced hyperpermeability is inhibited.

Further examinations showed that hyperpermeability can also be induced in human epithelial cells by microbial toxins. Thus, the incubation of human epithelial cells with 1 µg/ml of listeriolysin results in clear hyperpermeability. Surprisingly, however, it was found, that the hyperpermeability is inhibited with the addition of a peptide according to the invention, in particular 50 µg/ml of peptide SEQ ID No. 1.

Further examinations showed that an addition of 125 ng/ml of the toxin listeriolysin to human endothelial lung cells results in an increase in the content of phosphorylated myosin light chain. This effect is still enhanced by a toxin concentration of 250 ng/ml of listeriolysin. An addition of 62.5 ng/ml of the toxin pneumolysin to human endothelial lung cells also resulted in an increase in the relative content of phosphorylated myosin light chain. This effect was still enhanced by a toxin concentration of 125 ng/ml of pneumolysin. Surprisingly, however, it was found, that the addition of a peptide according to the invention, in particular 50 µg/ml of peptide SEQ ID No. 1, inhibits the phosphorylation of the myosin light chain caused by the toxins listeriolysin and pneumolysin.

Further examinations demonstrated that with the intratracheal application of toxins in mice, hyperpermeability of the lungs of mice is triggered, which was verified by the fact that Evans blue dye passes from the blood vessels into the lung tissue. Surprisingly, however, it was found, that with the intratracheal application of a peptide according to the invention, in particular 50 µg of peptide SEQ ID No. 1, there is an inhibition of the hyperpermeability caused by the toxin.

Further examinations showed that by triggering hyperpermeability in the lungs of mice, triggered by intratracheal application of toxin, e.g. 250 ng of pneumolysin, there is an increased number of leukocytes in the bronchoalveolar liquid. Surprisingly, however, it was found, that with the intratracheal application of a peptide according to the invention, in particular 50 µg of peptide SEQ ID No. 1, the toxin-related development of hyperpermeability is inhibited and clearly less leukocytes are present in the bronchoalveolar liquid in the lungs of mice.

Further examinations demonstrated that bacterial toxins result in a substantial increase in the content of activated protein kinase C alpha in human endothelial cells of the lungs. Surprisingly, however, it was found, that the addition of a peptide according to the invention, in particular of peptide SEQ ID No. 1, inhibits this toxin-mediated effect and thus results in an increase in the expression of the epithelial sodium channel. Surprisingly, it was also found, that an addition of the peptide according to the invention, in particular of peptide SEQ ID No. 1, to human epithelial cells results in a substantial increase in the expression of the epithelial sodium channel (ENaC). The invention will now be explained in more detail on the basis of the following examples and figures, to which it shall not be limited.

BRIEF DESCRIPTION OF THE DRAWINGS

For a more complete understanding of the present invention, and the advantages thereof, reference is now made to the following descriptions taken in conjunction with the accompanying drawings, in which:

FIG. 8 shows the change in the body weight of the test animals with viral pneumonia (group 1: negative control (PBS); group 2: positive control (influenza A via nasal); group 3: influenza A via nasal+10 µg of peptide SEQ ID No. 1 intratracheal).

FIG. 9 shows the change in the body temperature of test animals of these groups 1 to 3.

FIG. 10 shows the survival rate of test animals of these groups 1 to 3.

DETAILED DESCRIPTION OF THE INVENTION

EXAMPLES

Example 1A

Synthesis of a Peptide with the Amino Acid Sequence SEQ ID No. 1

A peptide with the amino acid sequence SEQ ID No. 1 was fully automatically synthesized using Fmoc solid phase synthesis with the following steps:

| Step | Process | Product |
|---|---|---|
| 1 | Coupling of the amino acids | Peptide bound to the solid phase |
| 2 | Split-off from the solid phase | Peptide in solution |
| 3 | Purification | Purified peptide as TFA salt |
| 4 | Purification/salt exchange | Purified peptide as acetate salt |
| 5 | Analytical examination | Purified peptide |

Subsequently, the peptide SEQ ID No. 1 was cyclized by oxidative formation of a disulfide bridge between the side chains of the amino acids cysteine (position 1) and cysteine (position 17).

Figure 1A:
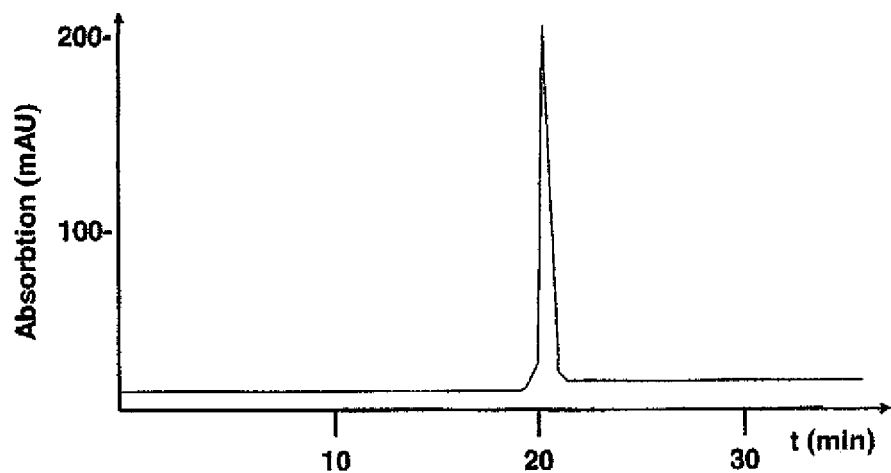
FIG. 1A shows the HPLC chromatogram of the protein with the amino acid sequence SEQ ID No. 1. Units: Y axis "Absorption in mAU"; X axis "Time in minutes".

Subsequently, the peptide was examined using reverse HPLC, wherein the result as shown in FIG. 1A was obtained. The purity of the peptide SEQ ID No. 1 was higher than 95%.

Example 1B

Synthesis of a Peptide with the Amino Acid Sequence SEQ ID No. 2

```
                                              SEQ ID No. 2
(NH2)Lys-Ser-Pro-Gly-Gln-Arg-Glu-Thr-Pro-Glu-Gly-
Ala-Glu-Ala-Lys-Pro-Trp-Tyr-Glu(COOH),
``` wherein an amide bond is formed between the amino group of the side chain of lysine Lys (1) and the carboxyl group of the side chain of glutamic acid Glu (19).

A peptide with the amino acid sequence SEQ ID No. 2 was fully automatically synthesized using Fmoc solid phase synthesis with the following steps:

| Step | Process | Product |
|---|---|---|
| 1 | Coupling of the amino acids | Peptide bound to the solid phase |
| 2 | Split-off from the solid phase | Peptide in solution |
| 3 | Purification | Purified peptide as TFA salt |
| 4 | Purification/salt exchange/ oxidative cyclization | Purified peptide as acetate salt |
| 5 | Analytical examination | Purified peptide |

The cyclization took place by the connection of the epsilon amino group of lysine (position 1) with the gamma carboxyl group of glutamic acid (position 19) forming an amide bond. This is achieved, for example, by transferring the gamma carboxyl group of the glutamine group into an active ester by means of dicyclohexylcarbodiimide (DHC), which active ester subsequently spontaneously reacts with the epsilon amino group of the lysine, forming a ring closure in the peptide.

Figure 1B:
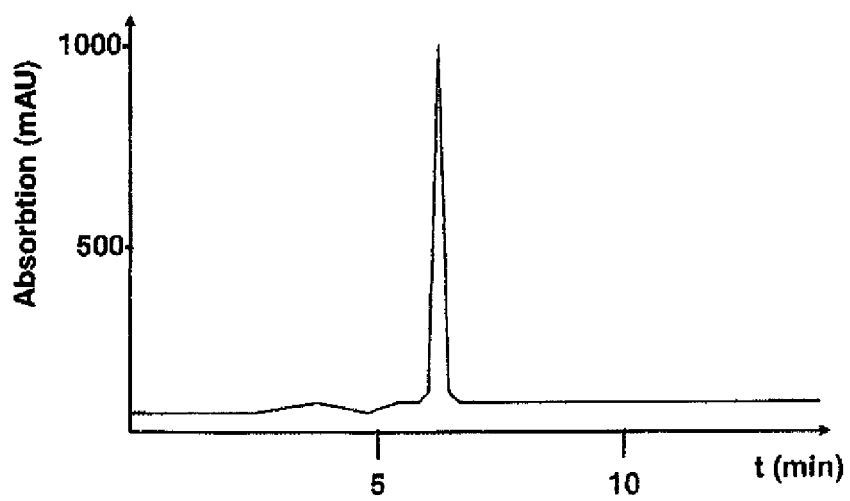
FIG. 1B shows the HPLC chromatogram of the protein with the amino acid sequence SEQ ID No. 2. Units: Y axis "Absorption in mAU"; X axis "Time in minutes".

Subsequently, the peptide was examined using reverse HPLC, wherein the result as shown in FIG. 1B was obtained. The purity of the peptide SEQ ID No. 2 was higher than 95%.

Example 1C

Synthesis of a Peptide with the Amino Acid Sequence SEQ ID No. 3

```
                                              SEQ ID No. 3
(NH2)Cys-Gly-Gln-Arg-Glu-Ala-Pro-Ala-Gly-Ala-Ala-
Ala-Lys-Pro-Trp-Tyr-Cys (COOH)

(NH2)Cys-Gly-Gln-Arg-Glu-Thr-Pro-Glu-Gly-Ala-Glu-
Ala-Lys-Pro-Trp-Tyr-Cys (COOH)
```

A peptide with the amino acid sequence SEQ ID No. 3 was fully automatically synthesized using Fmoc solid phase synthesis with the following steps:

| Step | Process | Product |
|---|---|---|
| 1 | Coupling of the amino acids | Peptide bound to the solid phase |
| 2 | Split-off from the solid phase | Peptide in solution |
| 3 | Purification | Purified peptide as TFA salt |
| 4 | Purification/salt exchange | Purified peptide as acetate salt |
| 5 | Analytical examination | Purified peptide |

Subsequently, the peptide SEQ ID No. 3 was cyclized by oxidative formation of a disulfide bridge between the side chains of the amino acids cysteine (position 1) and cysteine (position 17).

Figure 1C:
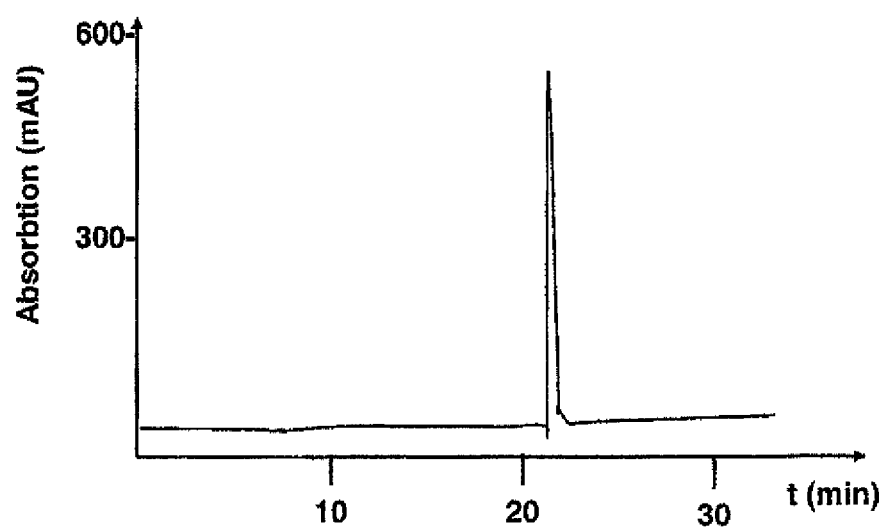
FIG. 1C shows the HPLC chromatogram of the protein with the amino acid sequence SEQ ID No. 3. Units: Y axis "Absorption in mAU"; X axis "Time in minutes".

Subsequently, the peptide was examined using reverse HPLC, wherein the result as shown in FIG. 1C was obtained. The purity of the peptide SEQ ID No. 3 was higher than 95%.

The difference between peptide SEQ ID No. 3 and peptide SEQ ID No. 1 consists in the fact that the amino acids Thr (6), Glu (8) and Glu (11) from peptide SEQ ID No. 1 are replaced by Ala (6), Ala (8) and Ala (11) in peptide SEQ ID No. 3.

Example 2

Influence of the Peptide SEQ ID No. 1 on Reactive Oxygen Molecules

Cell Culture of Endothelial Cells

The cell culture of endothelial cells took place with addition and without addition of 50 µg/ml of peptide SEQ ID No. 1 or with addition and without addition of 50 µg/ml of peptide SEQ ID No. 3, respectively.

For the generation of reactive oxygen molecules, arterial endothelial cells were cultivated in an oxygen-deficient gas mixture of 0.1% oxygen, 5% carbon monoxide and 94.9% nitrogen (hypoxic gas mixture). In control experiments, the gas concentrations were 21% oxygen, 5% carbon monoxide and 74% nitrogen (normoxic gas mixture).

After 90 minutes under oxygen-deficient conditions, the endothelial cells were cultivated with 21% oxygen for a further 30 minutes. Thereafter, 20 µl of a solution consisting of 20 uM 1-hydroxy-3-methoxycarbonyl-2,2,5,5-tetramethylpyrrolidine HCl (CHM), 20 µM DPBS, 25 µM desferrioxamine and 5 µM diethyldithiocarbamate as well as 2 µl of DMSO were added to the cells.

Trypsinization of the Cells.

Following cell culture, the cells were individualized in a manner common in the laboratory by adding a trypsin solution. The endothelial cells were washed and suspended in 35 µl of a solution consisting of DPBS and 25 µM desferrioxamine and 5 µM diethyldithiocarbamate.

Measurement of the Electron Paramagnetic Resonance (EPR)

The determination of the electron paramagnetic resonance (EPR), also called electron spin resonance, serves the investigation of paramagnetic substances, e.g. for detection of unpaired electrons in reactive oxygen molecules (radicals of the oxygen).

For that, the previously treated cells were placed into 50 µl capillaries and examined in a MiniScope MS200 ESR of the company Magnettech (Berlin, Germany) at 40 mW microwaves, 3000 mG modulation amplitude, 100 kHz modulation frequency.

Figure 2A:
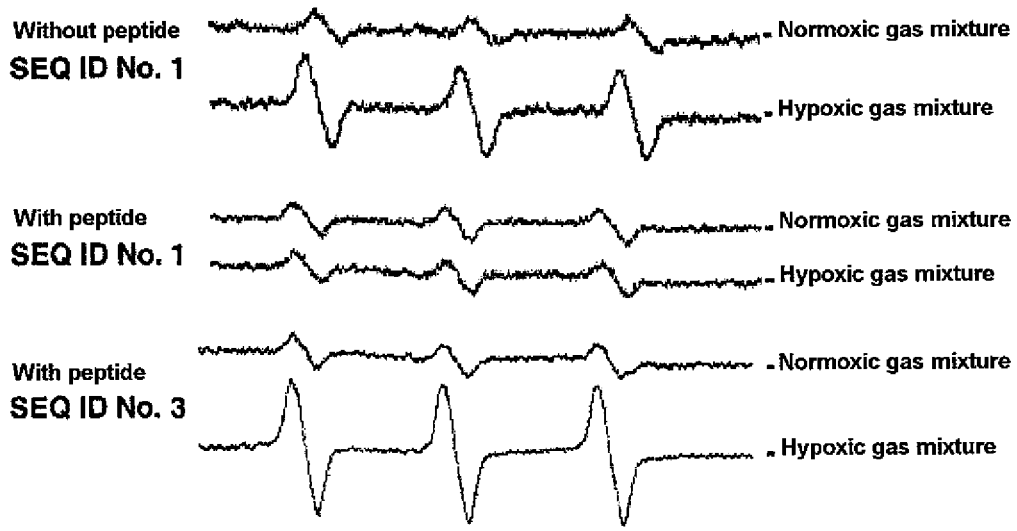
FIG. 2A shows the electron paramagnetic resonance (EPR) spectra of endothelial cells, which were cultivated at either 21% oxygen (normoxic gas mixture) or 0.1% oxygen (hypoxic gas mixture) with and without the addition of peptide SEQ ID No. 1 or peptide SEQ ID No. 3, respectively.
Figure 2B:
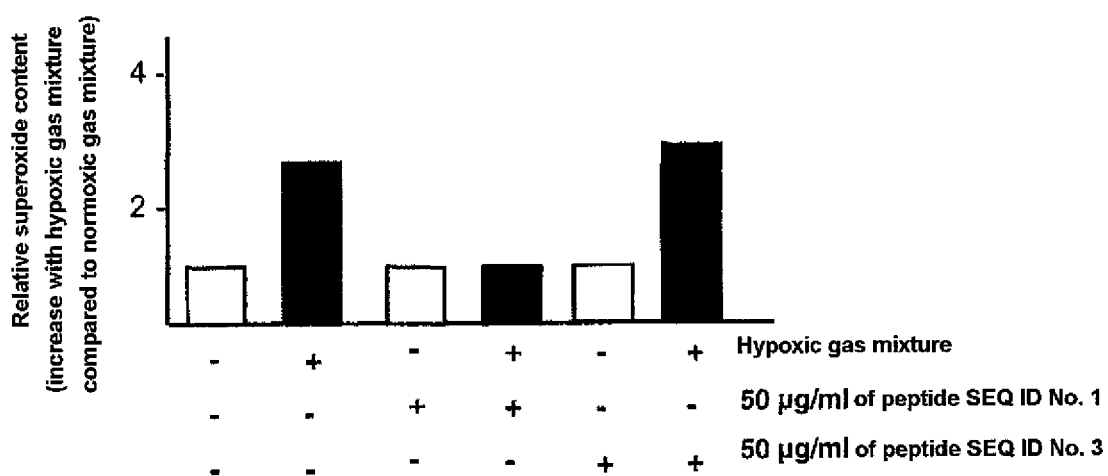
FIG. 2B shows the relative content of reactive oxygen molecules (superoxide) in endothelial cells, which were cultivated at either 21% oxygen (normoxic gas mixture) or 0.1% oxygen (hypoxic gas mixture) with and without the addition of peptide SEQ ID No. 1, or at 0.1% oxygen (hypoxic gas mixture) with and without the addition of peptide SEQ ID No. 3.

As FIGS. 2A and 2B show, with a normal oxygen concentration of 21% (normoxic gas mixture), there only is a low formation of reactive oxygen molecules. Under oxygen deficiency (0.1% oxygen, hypoxic gas mixture), there is a 3-fold higher formation of reactive oxygen molecules. If, however, the peptide SEQ ID No. 1 is added to endothelial cells cultivated under oxygen deficiency (oxygen content 0.1%, hypoxic gas mixture), then no reactive oxygen molecules are formed by the endothelial cells.

Contrary to peptide SEQ ID No. 1, an addition of peptide SEQ ID No. 3 to endothelial cells cultivated under oxygen deficiency (oxygen content 0.1%, hypoxic gas mixture), does not result in an inhibition of the formation of reactive oxygen molecules by the endothelial cells.

The difference between peptide SEQ ID No. 3 and peptide SEQ ID No. 1 is that the amino acids Thr (6), Glu (8) and Glu (11) of peptide SEQ ID No. 1 are replaced with Ala (6), Ala (8) and Ala (11) in SEQ ID No. 3.

Example 3

Inhibition of Hyperpermeability in Endothelial Cells and Epithelial Cells by the Peptide SEQ ID No. 1

Materials

Human epithelial cells of the lungs of type H441 were acquired from the company ATTC.

Human endothelial cells of the lungs, isolated from capillaries of the lungs, were acquired from the company Lonza.

The microbial toxins listeriolysin (LLO) and pneumolysin (PLY) were acquired from the University of Giessen.

Cell Culture

Human endothelial cells of the lungs, isolated from capillaries of the lungs, were cultivated in a manner common in the laboratory.

Epithelial cells of the lungs of type H441 were cultivated in a manner common in the laboratory in a commercial RPMI 1640 medium with the additives 2 mM L-glutamine, 1.5 g/l of sodium carbonate, 4.5 g/l of glucose, 10 mM HEPES buffer pH 7.4, 10% bovine serum. The ECIS experiments took place in serum-free medium.

Hyperpermeability

In order to cause hyperpermeability, i.e. injuries of the endothelial cells and epithelial cells, the human epithelial cells of the lungs as well as the human endothelial cells of the lungs were cultivated in a manner common in the laboratory up to the formation of a continuous cell layer, and subsequently, the toxins listeriolysin or pneumolysin, respectively, were added.

Determination of the Transendothelial Resistance

Before, during and after the addition of the microbial toxins pneumolysin and listeriolysin to human endothelial cells, the electric resistance of the cell layer (transendothelial resistance) was determined by means of electrical cell-substrate impedance analysis.

Figure 3A:
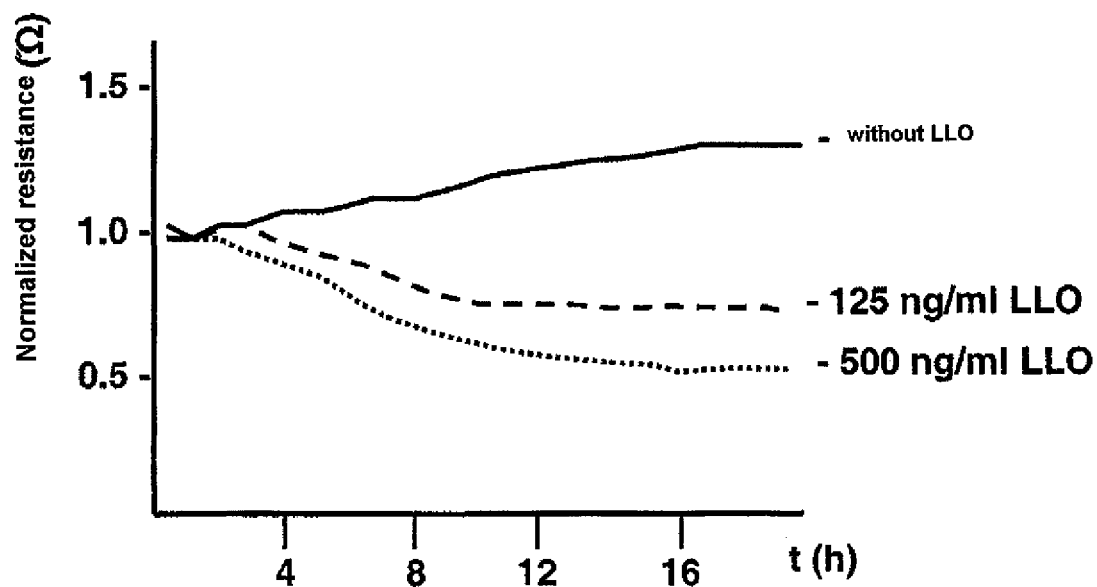
FIG. 3A shows the course of the electric resistance of human epithelial cells of the lungs without addition of the toxin listeriolysin as well as following addition of 125 ng/ml of listeriolysin (125 ng/ml of LLO) and following addition of 500 ng/ml of listeriolysin (500 ng/ml of LLO).

As FIG. 3A shows, the electric resistance decreases with an addition of 125 ng/ml of listeriolysin to cultivated human endothelial cells. Hyperpermeability is developed. This effect is even more significant with a higher amount of 500 ng/ml of listeriolysin.

Figure 3B:
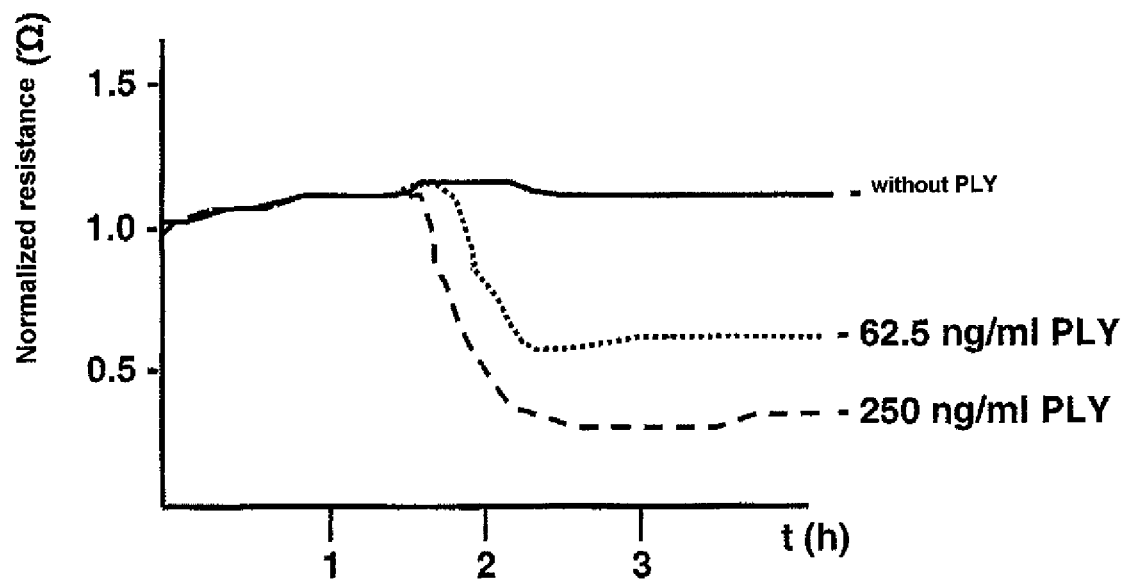
FIG. 3B shows the course of the electric resistance of human epithelial cells of the lungs without addition of the toxin pneumolysin as well as following addition of 62.5 ng/ml of pneumolysin (62.5 ng/ml of PLY) and following addition of 250 ng/ml of pneumolysin (250 ng/ml of PLY).

As FIG. 3B shows, the electric resistance decreases with an addition of 62.5 ng/ml of pneumolysin to cultivated human endothelial cells. Hyperpermeability is developed. This effect is even more significant with a higher amount of 250 ng/ml of pneumolysin.

Figure 3C:
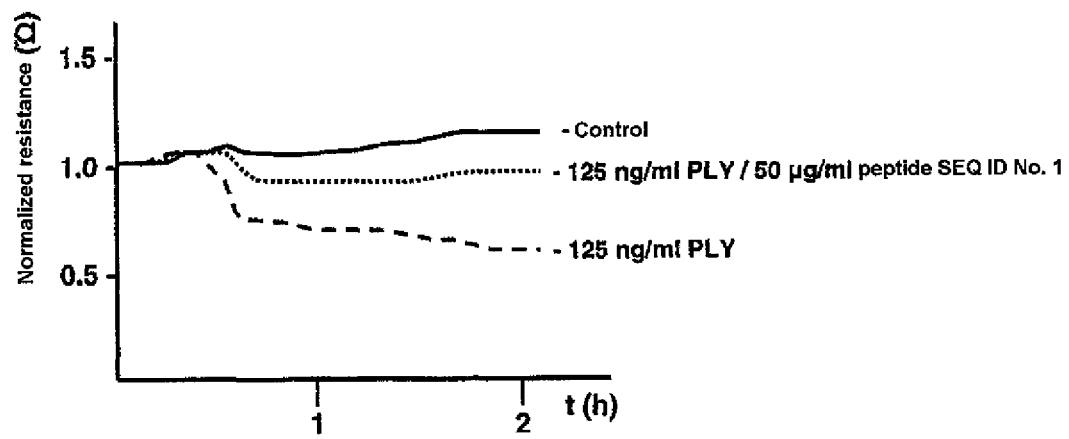
FIG. 3C shows the course of the electric resistance of human epithelial cells of the lungs without addition of the toxin pneumolysin/peptide SEQ ID No. 1 (control) as well as following addition of 125 ng/ml of pneumolysin (125 ng/ml of PLY) as well as following addition of 125 ng/ml of pneumolysin/50 µg/ml of peptide SEQ ID No. 1 (125 ng/ml of PLY/50 µg/ml of peptide SEQ ID No. 1).

As FIG. 3C shows, the electric resistance decreases with an addition of 125 ng/ml of pneumolysin to cultivated human endothelial cells. Hyperpermeability is developed. However, the hyperpermeability caused by the addition of the toxin pneumolysin is inhibited by addition of 50 µg/ml of peptide SEQ ID No. 1.

Figure 3D:
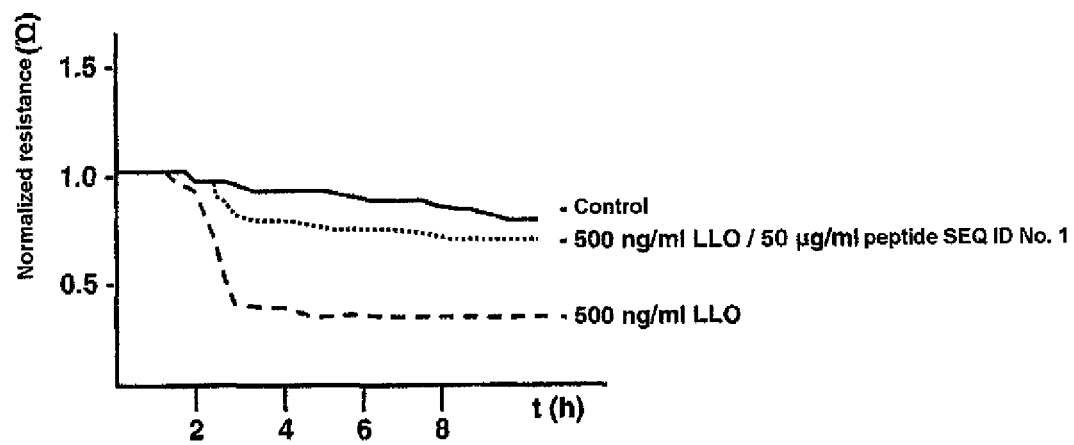
FIG. 3D shows the course of the electric resistance of human epithelial cells of the lungs without addition of the toxin listeriolysin/peptide SEQ ID No. 1 (control) as well as following addition of 500 ng/ml of listeriolysin (500 ng/ml of LLO) as well as following addition of 500 ng/ml of listeriolysin/50 µg/ml of peptide SEQ ID No. 1 (500 ng/ml of LLO/50 µg/ml of peptide SEQ ID No. 1).

As FIG. 3D shows, the electric resistance decreases with an addition of 500 ng/ml of listeriolysin to cultivated human endothelial cells. Hyperpermeability is developed. However, the hyperpermeability caused by the addition of the toxin listeriolysin is inhibited by addition of 50 µg/ml of peptide SEQ ID No. 1.

Figure 3E:
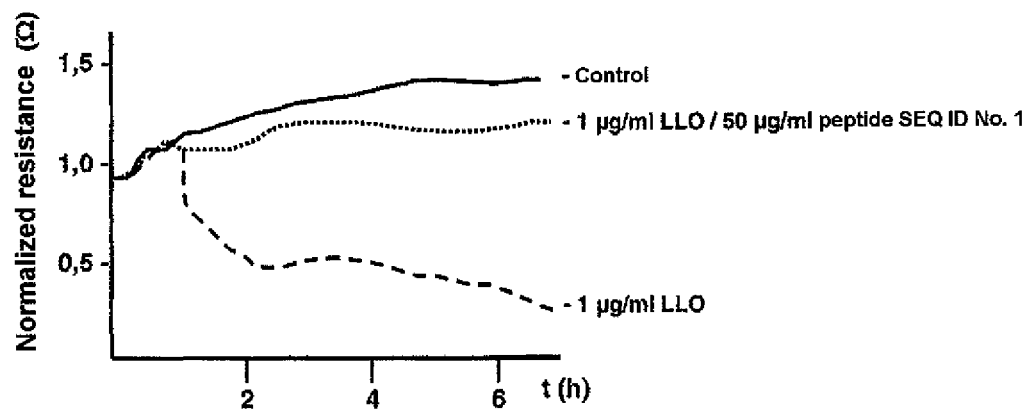
FIG. 3E shows the course of the electric resistance of human epithelial cells of the lungs without addition of the toxin listeriolysin/peptide SEQ ID No. 1 (control) as well as following addition of 1 µg/ml of listeriolysin (1 µg/ml of LLO) as well as following addition of 1 µg/ml of listeriolysin/50 µg/ml of peptide SEQ ID No. 1 (1 µg/ml of LLO/50 µg/ml of peptide SEQ ID No. 1).
Figure 7:
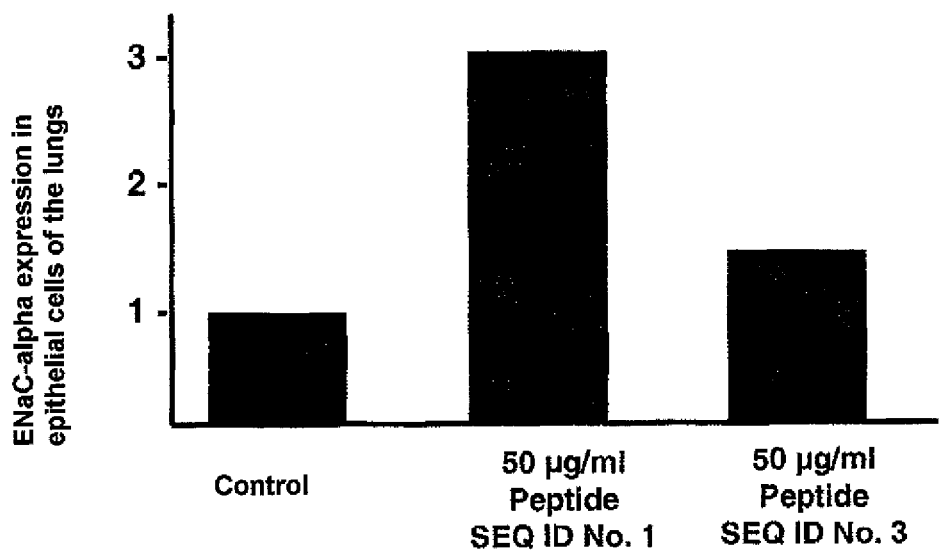
FIG. 7 shows the expression of the epithelial sodium channel (ENaC) in human epithelial lung cells compared to cell culture conditions without and following addition of 50 µg/ml of peptide SEQ ID No. 1 as well as following addition of 50 µg/ml of peptide SEQ ID No. 3. The content of mRNS for ENaC was determined using "real-time PCR".

As FIG. 3E shows, the electric resistance decreases with an addition of 1 µg/ml of listeriolysin to cultivated human epithelial cells. Hyperpermeability is developed. However, the hyperpermeability caused by the addition of the toxin listeriolysin is inhibited by addition of 50 µg/ml of peptide SEQ ID No. 1.

Example 4

Inhibition of the Phosphorylation of the Myosin Light Chain by the Peptide SEQ ID No. 1

Materials

Human endothelial cells of the lungs, isolated from capillaries of the lungs, were acquired from the company Lonza.

The microbial toxins listeriolysin (LLO) and pneumolysin (PLY) were acquired from the University of Giessen.

Cell Culture

Human endothelial cells of the lungs, isolated from capillaries of the lungs, were cultivated in a manner common in the laboratory.

Determination of Phosphorylation of the Myosin Light Chain

For the determination of phosphorylation of the myosin light chain and the influence of the peptide SEQ ID No. 1 on the phosphorylation, the previously cultivated human endothelial cells of the lungs were washed with phosphate buffer pH 7.4, which contained 1 mM orthovanadate. The cell contents was lysed by incubation of the cells with a solution of 20 mM tris buffer (pH 7.4), 150 mM mol/l of NaCl, 1 mM EDTA, 1 mM EGTA, 1% Triton X-100, 2.5 mM sodiumpyrophosphate, 1 mM betaglycerophosphate, 1 mM sodiumvanadate, 1 µg/ml of leupeptine, 1 mM phenylmethylsulfonylfluoride. In addition, the cells were digested with ultrasound. The cell lysate was centrifuged in order to obtain the soluble components. The soluble cell lysate was subsequently applied to denaturing sodium dodecyl sulfate polyacrylamide gel electrophoresis in a manner common in the laboratory, and the proteins were separated according to their masses. Thereafter, the proteins were transferred onto nitrocellulose membranes. The protein blots were treated with a solution of 0.1% Tween 20 and 5% dry milk powder for 1 hour in a manner common in the laboratory. Subsequently, the protein blots were incubated with antibodies directed against either the myosin light chain or the phosphorylated myosin light chain.

In order to make either the myosin light chain or the phosphorylated myosin light chain visible, the antibodies were made visible on diagnostic film using chemiluminescence in a manner common in the laboratory. The signal strength was determined with densitometry, and the ratio of myosin light chain to phosphorylated myosin light chain was determined.

Figure 4A:
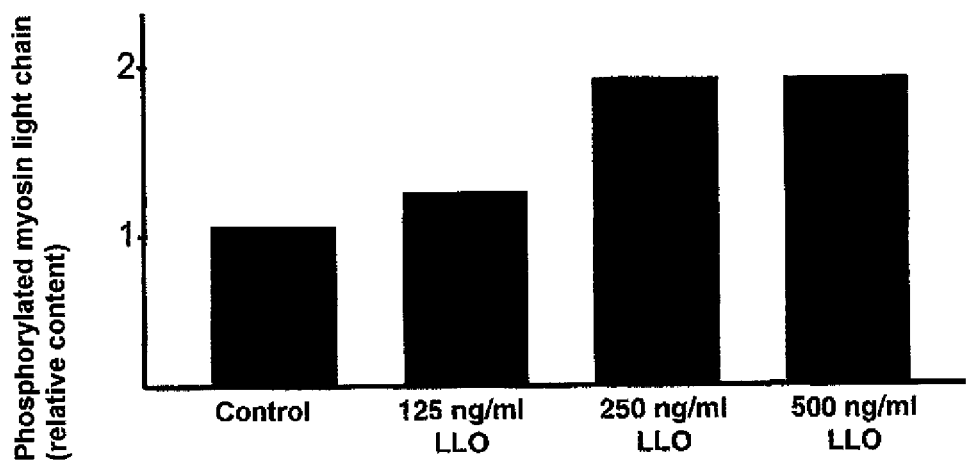
FIG. 4A shows the relative content of phosphorylated myosin light chain in human endothelial cells of the lungs depending on the concentration of the toxin listeriolysin (125 ng/ml of LLO, 250 ng/ml of LLO, 500 ng/ml of LLO).

As FIG. 4A shows, an addition of 125 ng/ml of the toxin listeriolysin to human endothelial lung cells results in an increase in the relative content of phosphorylated myosin light chain. This effect is still enhanced by a toxin concentration of 250 ng/ml of listeriolysin.

Figure 4B:
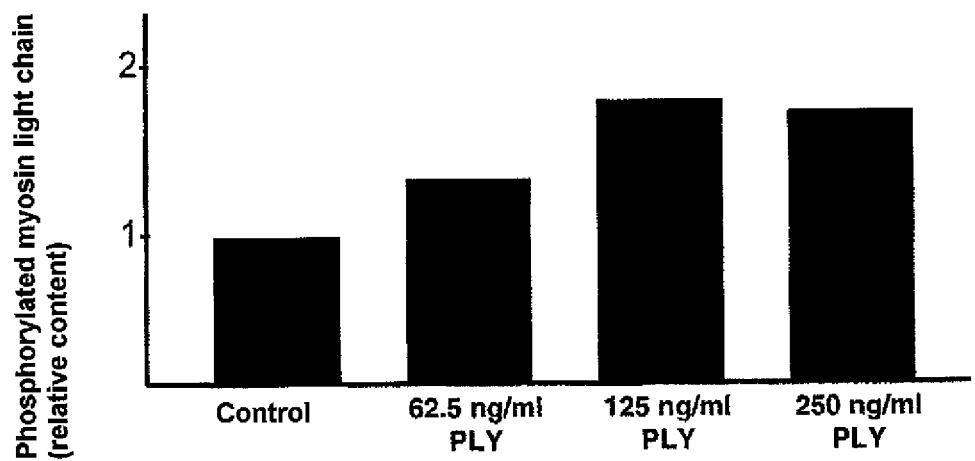
FIG. 4B shows the relative content of phosphorylated myosin light chain in human endothelial cells of the lungs depending on the concentration of the toxin pneumolysin (62.5 ng/ml of PLY, 125 ng/ml of PLY, 250 ng/ml of PLY).

As FIG. 4B shows, an addition of 62.5 ng/ml of the toxin pneumolysin to human endothelial lung cells results in an increase in the relative content of phosphorylated myosin light chain. This effect is still enhanced by a toxin concentration of 125 ng/ml of pneumolysin.

Figure 4C:
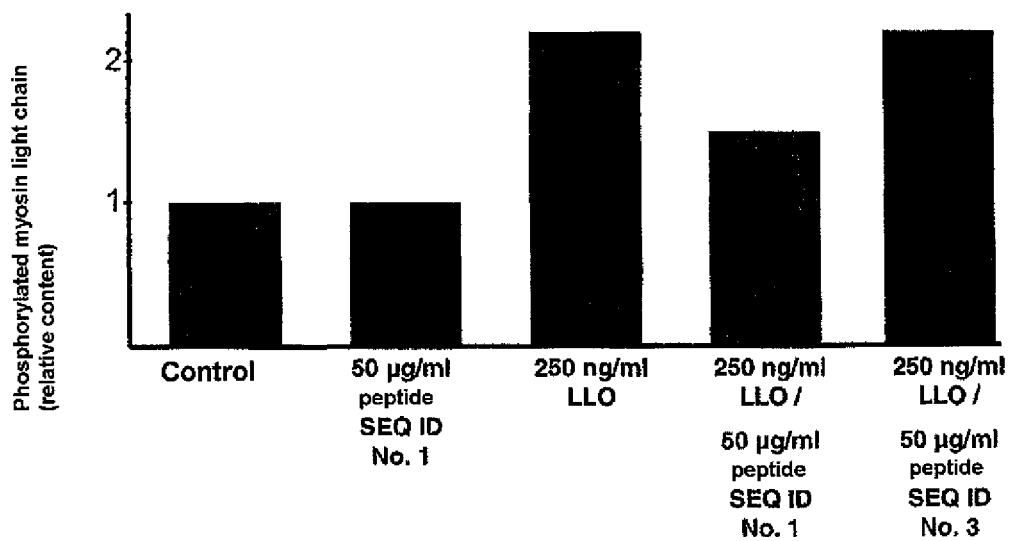
FIG. 4C shows the relative content of phosphorylated myosin light chain in human endothelial cells of the lungs depending on the addition of 50 µg/ml of peptide SEQ ID No. 1, 250 ng/ml of the toxin listeriolysin (LLO), 50 µg/ml of peptide SEQ ID No. 1/250 ng/ml of the toxin listeriolysin (LLO), 50 µg/ml of peptide SEQ ID No. 3/250 ng/ml of the toxin listeriolysin (LLO).

As FIG. 4C shows, an addition of 125 ng/ml of the toxin listeriolysin to human endothelial lung cells results in an increase in the relative content of phosphorylated myosin light chain. An addition of 50 µg/ml of peptide SEQ ID No. 1 has no influence on the content of phosphorylated myosin light chain. The increase in the content of phosphorylated myosin light chain by 250 ng/ml of the toxin listeriolysin is inhibited by an addition of 50 µg/ml of peptide SEQ ID No. 1. A peptide SEQ ID No. 3 has no influence on the increase in the content of phosphorylated myosin light chain mediated by the toxin listeriolysin.

Figure 4D:
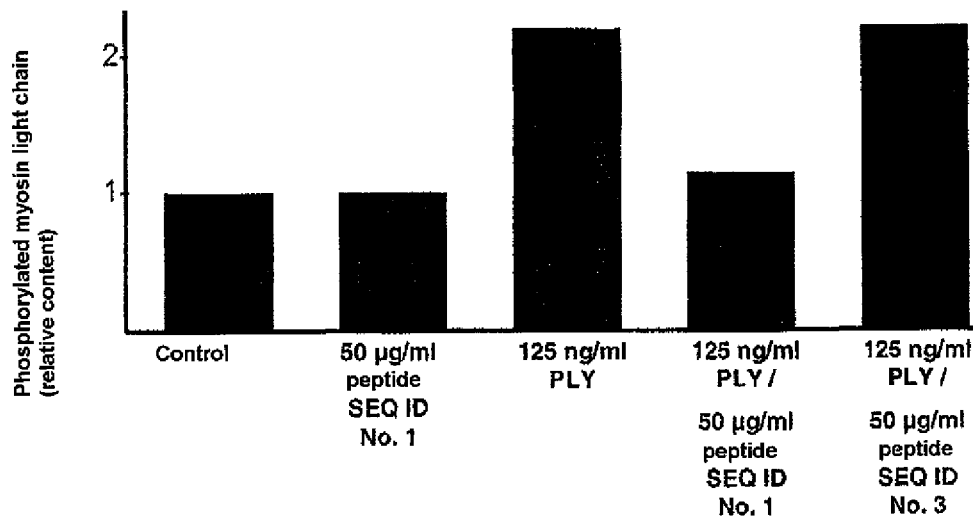
FIG. 4D shows the relative content of phosphorylated myosin light chain in human endothelial cells of the lungs depending on the addition of 50 µg/ml of peptide SEQ ID No. 1, 125 ng/ml of the toxin pneumolysin (PLY), 50 µg/ml of peptide SEQ ID No. 1/125 ng/ml of the toxin pneumolysin (PLY), 50 µg/ml of peptide SEQ ID No. 3/125 ng/ml of the toxin pneumolysin (PLY).

As FIG. 4D shows, an addition of 125 ng/ml of the toxin pneumolysin to human endothelial lung cells results in an increase in the relative content of phosphorylated myosin light chain. An addition of 50 µg/ml of peptide SEQ ID No. 1 has no influence on the content of phosphorylated myosin light chain. The increase in the content of phosphorylated myosin light chain by 125 ng/ml of the toxin pneumolysin is inhibited by an addition of 50 µg/ml of peptide SEQ ID No. 1. A peptide SEQ ID No. 3 has no influence on the increase in the content of phosphorylated myosin light chain mediated by the toxin pneumolysin.

The difference between peptide SEQ ID No. 3 and peptide SEQ ID No. 1 is that the amino acids Thr (6), Glu (8) and Glu (11) of peptide SEQ ID No. 1 are replaced with Ala (6), Ala (8) and Ala (11) in SEQ ID No. 3.

Example 5

Influence of the Peptide SEQ ID No. 1 on Hyperpermeability and Acute Lung Damage in an Animal Model Induction of Hyperpermeability in Mice Laboratory mice were intratrachealy treated with a mixture of isoflurane/oxygen prior to preparation of the lungs, as well as with 100 µl per mouse of a mixture of ketamine/rompun (1.33:1). Following anesthesia, a venous catheter was implanted into the mice. For induction of hyperpermeability of the lungs, 25 µl of liquid were subsequently nebulized into the lungs with a fine syringe. The liquid either contained 0.9% saline solution or 250 ng of the toxin pneumolysin or 250 ng/ml of pneumolysin/50 µg/ml of peptide SEQ ID No. 1.

Visualization of Hyperpermeability by Evans Blue 5.5 hours following administration of the toxin pneumolysin, Evans blue dye, dissolved in 0.9% saline solution, was intravenously applied to the mice at 100 mg/kg of mouse weight. After 30 minutes, blood was withdrawn from the animals by means of heart puncture. Subsequently, the lungs were removed, washed with 1 ml of EDTA phosphate buffer (pH 7.4), and quick-frozen in liquid nitrogen. For determination of the Evans blue dye content in the lung tissue, the lungs were then homogenized in cold phosphate buffer (1 ml of buffer per 100 mg of lung tissue), incubated with formalin solution for 18 hours, and subsequently centrifuged (5,000× g, 30 minutes). In the liquid supernatant, the absorptions were then determined photometrically at 620 nm and at 740 nm. The Evans blue dye content in the lung tissue was determined on the basis of a reference curve for Evans blue dye dissolved in formalin solution, deducting the content of hemoglobin pigments. The discharge of Evans blue dye from the capillaries into the lung tissue due to hyperpermeability induced by the toxin pneumolysin was compared to the amount of dye in the blood serum.

Figure 5A:
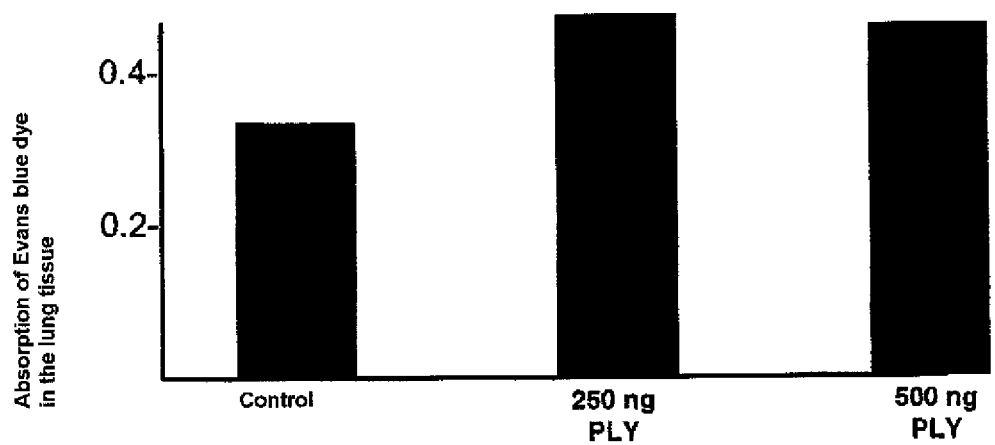
FIG. 5A shows the content of Evans blue dye in the lung tissue of mice 5.5 hours following intratracheal administration of the toxin pneumolysin with the doses 250 ng of pneumolysin per mouse (250 ng of PLY) and 500 ng of pneumolysin per mouse (500 ng of PLY).

As FIG. 5A shows, an intratracheal application of the toxin pneumolysin with doses of 250 ng and 500 ng per mouse results in hyperpermeability, which is determined by the fact that blood with the Evans blue dye passes from the lung capillaries into the lung tissue and can be verified in the lung tissue.

Figure 5B:
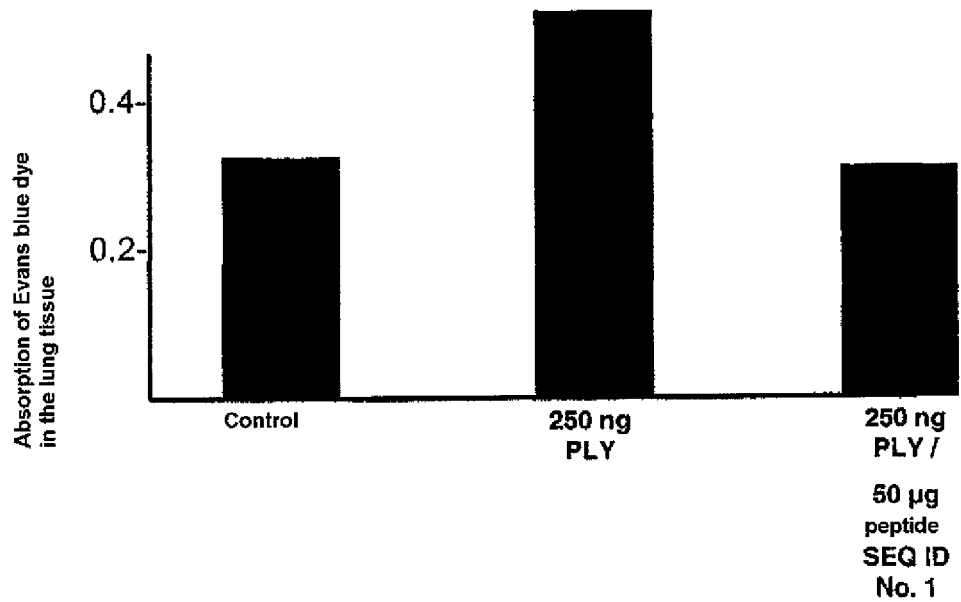
FIG. 5B shows the content of Evans blue dye in the lung tissue of mice 5.5 hours following intratracheal administration of 250 ng of the toxin pneumolysin per mouse as well as following intratracheal administration of 250 ng of the toxin pneumolysin and 50 µg of peptide SEQ ID No. 1 per mouse.

As FIG. 5B shows, an intratracheal application of the toxin pneumolysin with a dose of 250 ng per mouse results in hyperpermeability, which is determined by the fact that blood with the Evans blue dye passes from the lung capillaries into the lung tissue and can be verified in the lung tissue. With the intratracheal application of 50 µg of peptide SEQ ID No. 1, there is an inhibition of the toxin-mediated development of hyperpermeability.

Figure 5C:
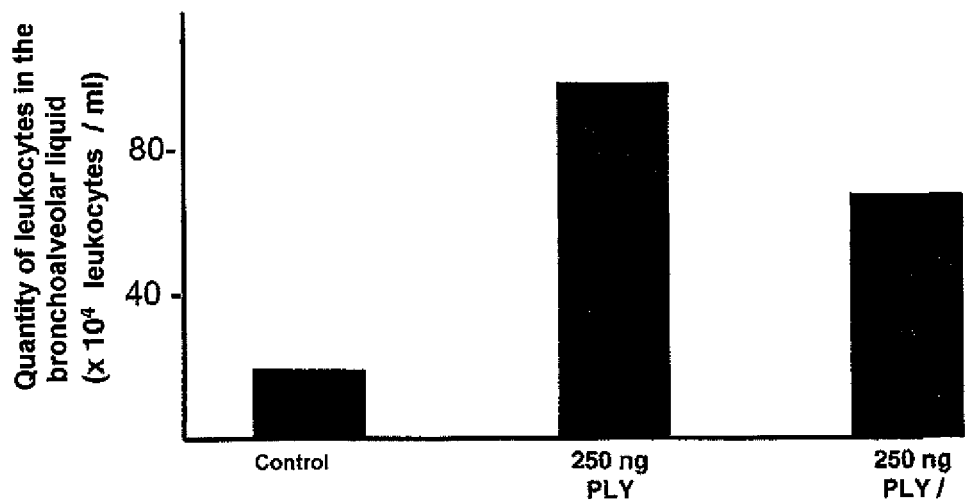
FIG. 5C shows the content of leukocytes in the bronchoalveolar liquid in the lungs of mice 5.5 hours following intratracheal administration of 250 ng of the toxin pneumolysin per mouse as well as following intratracheal administration of 250 ng of the toxin pneumolysin and 50 µg of peptide SEQ ID No. 1 per mouse.

As FIG. 5C shows, an intratracheal application of the toxin pneumolysin with a dose of 250 ng per mouse results in an increased number of leukocytes in the bronchoalveolar liquid of the lungs in mice due to the development of hyperpermeability. With the intratracheal application of 50 µg of peptide SEQ ID No. 1, there is an inhibition of the toxin-mediated development of hyperpermeability and a clear reduction in the number of leukocytes in the broncho-alveolar liquid in the lungs of mice.

Example 6

Inhibition of the Activation of Protein Kinase C by the Peptide SEQ ID No. 1

Figure 6:
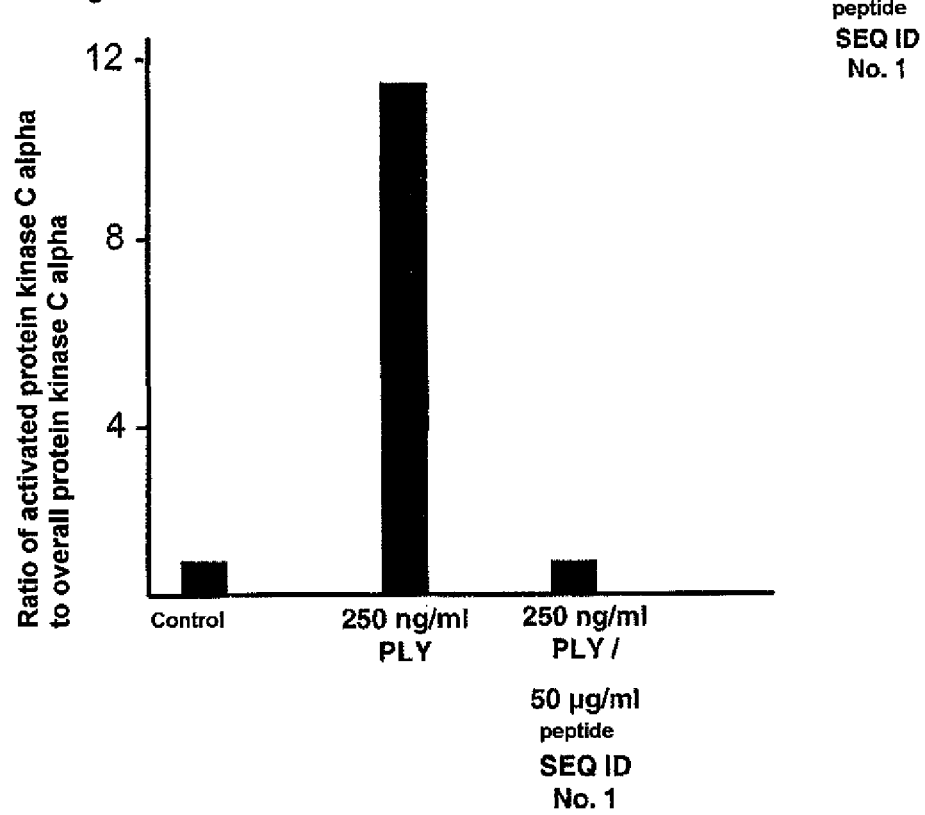
FIG. 6 states the content of activated protein kinase C alpha in relation to the overall content of protein kinase C alpha, depending on the incubation of human endothelial lung cells with 250 ng/ml of the toxin pneumolysin (250 ng/ml of PLY) and the mixture of 250 ng/ml of the toxin pneumolysin and 50 µg/ml of peptide SEQ ID No. 1 (250 ng/ml of PLY/50 µg/ml of peptide SEQ ID No. 1).

Materials
Human endothelial cells of the lungs, isolated from capillaries of the lungs, were acquired from the company Lonza.
The microbial toxin pneumolysin (PLY) was acquired from the University of Giessen.
Cell Culture
Human endothelial cells of the lungs, isolated from capillaries of the lungs, were cultivated in a manner common in the laboratory. During cell culture, the toxin pneumolysin was added with a concentration of 250 ng/ml, or the toxin pneumolysin with a concentration of 250 ng/ml and the peptide SEQ ID No. 1 with a concentration of 50 μg/ml.
Determination of the Content of Activated Protein Kinase C Alpha
The content of activated protein kinase C alpha was determined by ELISA measurement using an antibody directed against the activated protein kinase C alpha (phospho-threonine 638 protein kinase C alpha). Simultaneously, the overall content of protein kinase C alpha was determined using a commercially available ELISA assay.
As FIG. 6 shows, due to the effect of the toxin pneumoly sin, there is a strong increase in the content of activated protein kinase C alpha compared to the overall concentration of protein kinase C alpha. With the addition of peptide SEQ ID No. 1, there is an inhibition of the activation of protein kinase C alpha Example 7

Increase in the Expression of the Epithelial Sodium Channel (ENaC) in Epithelial Cells by the Peptide SEQ ID No. 1

Materials
Human epithelial cells of the lungs of type H441 were acquired from the company ATTC.
Cell Culture
Epithelial cells of the lungs of type H441 were cultivated in a manner common in the laboratory in a commercial RPMI 1640 medium with the additives 2 mM L-glutamine, 1.5 g/l of sodium carbonate, 4.5 g/l of glucose, 10 mM HEPES buffer pH 7.4, 10% bovine serum.
Verification of the Expression of the Epithelial Sodium Channel
In the cultivated epithelial cells, the expression of the sodium channel (ENaC) was determined by means of "real-time PCR". These examination took place in cells without and with the addition of 50 ug/ml of peptide SEQ ID No. 1, as well as following the addition of 50 μg/ml of peptide SEQ ID No. 3.
As examination 7 shows, with the addition of 50 ug/ml of peptide SEQ ID No. 1 to epithelial cells of the lungs, there is a triplication of the expression of the sodium channel ENaC.
With an addition of 50 μg/ml of peptide SEQ ID No. 3, there is no substantial increase in the expression of the sodium channel ENaC.
The difference between peptide SEQ ID No. 3 and peptide SEQ ID No. 1 consists in the fact that the amino acids Thr (6), Glu (8) and Glu (11) from peptide SEQ ID No. 1 are replaced by Ala (6), Ala (8) and Ala (11) in peptide SEQ ID No. 3.

Example 8

Effect of Peptide SEQ ID No. 1 on the Course of Disease in Mice with Viral Lung Infection The following animal study groups were examined in respect of the effect of peptide SEQ ID No. 1 on a viral lung infection:
Group 1. Negative control (PBS via nasal).
Group 2. Positive control (infection with approx. 2,000 units of influenza A virus via nasal).
Group 3. Test group (infection with approx. 2,000 units of influenza A virus via nasal, as well as intratracheal administration of 10 μg of peptide SEQ ID No. 1).
In each group, 6 BALB/c mice were used.
The following treatment scheme was followed:
Day of treatment 0:
Group 1: Administration of PBS via nasal.
Group 2: Infection of the mice with influenza virus A via nasal.
Group 3: Infection of the mice with influenza virus A via nasal and administration of peptide SEQ ID No. 1.
Days of treatment 0, 2, 4, 6, 8:
Group 1: Intratracheal administration of PBS.
Group 2: Intratracheal administration of PBS.
Group 3: Intratracheal administration of peptide SEQ ID No. 1.
Days of treatment 0 to 10:
Daily observation of body temperature, body weight and survival rate of the test animals.
The examinations demonstrated that test animals with viral lung infection (group 2) lost approx. 20% of their body weight within 10 days.
Compared to that, the body weight of the test animals reduced by only approx. 10%, when the peptide SEQ ID No. 1 was administered (group 3).
The results are shown in FIG. 8.
The examinations furthermore demonstrated, that in the test animals with viral lung infection (group 2), the body temperature cooled down from 37.5° C. to 33° C. after 7 days. Subsequently, the body temperature increased to 35° C.
Compared to that, in the test animals with administration of peptide SEQ ID No. 1 (group 3), it only reduced to 35° C. after 7 days. Subsequently, the body temperature increased to 37° C. again.
The results are shown in FIG. 9.
The examinations furthermore demonstrated, that 10 days after the viral lung infection, ⅔ of the test animals of group 2 had died.
Compared to that, the mortality of the test animals with administration of peptide SEQ ID No. 1 (group 3) after 10 days was only ⅓.
The results are shown in FIG. 10.
In total, the examinations of test animals with viral lung infection show that the administration of peptide SEQ ID No. 1 reduces the decrease in body weight, reduces the lowering of the body temperature and results in a clearly increased survival rate.

Example 9

Application of Peptide SEQ ID No. 1 ("AP301") in a Lavage-Induced Large Animal ARDS Model Material & methods: With the consent of the competent animal protection commission, lung damage was induced in two pigs (25 kg) under general anesthesia by surfactant depletion (four-time bronchoalveolar lavage, 30 ml/kg of body weight each). Subsequently, 1 mg/kg of body weight AP301 (peptide SEQ ID No. 1) was endotracheally applied. Animal 1 (1) received a deep tracheal injection of the overall dose, while for animal 2 (2), nebulization of the same dosage over 30 min was performed. Thereafter, there was a five-hour ventilation period. The arterial oxygen partial pressure ($paO_2$) was recorded using an intra-aortic real-time measuring probe (FOXY, Ocean Optics, USA) validated in advance. Spirometry and hemodynamics were permanently registered as well as measurements with the PiCCO technology performed at half-hour intervals.

Results: During application of the drug, no undesired hemodynamic effects were demonstrated. The ventilation settings were constantly kept in the non-protective range (Pmax 40 mbar, tidal volume≥10 ml/kg of body weight, PEEP≤10 mbar, frequency 25-35/min) in order to avoid therapeutic effects. Both animals showed continuous improvement of oxygenation limited to about 1.5 hours with a $paO_2$ increase by max. 162.8 mmHg (1) or 224.6 mmHg (2), respectively. With nebulization of AP301, this occurred delayed compared to the deep tracheal application, however, it was more pronounced. In parallel to the improvement of gas exchange, a reduction of the extra-vascular lung water by 15.8-52.5% compared to the initial value could be registered following surfactant depletion.

These results impressively show that the new pharmacological effect approach for treatment of ARDS according to the invention also proves to be efficient in the approved large animal model for treatment of ARDS.

SUMMARY OF THE SEQUENCES

| Sequence | ID |
|---|---|
| CGQRETPEGAEAKPWYC | SEQ ID No. 1 |
| KSPGGQRETPEGAEAKPWYE | SEQ ID No. 2 |
| CGQREAPAGAAAKPWYC | SEQ ID No. 3 |
| TPEGAE | SEQ ID No. 4 |
| QRETPEGAEAKPWY | SEQ ID No. 5 |
| PKDTPEGAELKPWY | SEQ ID No. 6 |
| CGPKDTPEGAELKPWYC | SEQ ID No. 7 |
| CGQKETPEGAEAKPWYC | SEQ ID No. 8 |
| CGQRETPEGAEARPWYC | SEQ ID No. 9 |
| CGQRETPEGAEAKPC | SEQ ID No. 10 |
| CQRETPEGAEAKPWYC | SEQ ID No. 11 |
| CGQRETPEGAEAKFWYC | SEQ ID No. 12 |

The invention claimed is:

1. A method of preventing edemas by decreasing hyperpermeability due to damage to endothelial and epithelial layers comprising:
   identifying a patient in need of prevention of edema prior to an onset of lung edema, wherein the patient in need of prevention of edema is selected from the group of patients with pneumonia caused by an infection with bacteria, viruses, mycoplasmas, protozoa, worms or fungi, toxically or immunologically caused pneumonias, pneumonias caused by inhalation of toxic substances or radiation; bacterial lung diseases, or viral lung diseases; and
   administering an efficient amount of a peptide with SEQ ID NO. 1 (CGQRETPEGAEAKPWYC) to a patient to prevent lung edemas by decreasing hyperpermeability prior to damage to the endothelial and epithelial layers.

2. The method of claim 1, wherein the peptide is cyclized via a disulfide bridge between said C residues.

3. The method of claim 1, wherein the cells of the endothelial layers are protected against hyperpermeability triggered by reactive oxygen molecules.

4. The method of claim 1, wherein the cells of the endothelial layers are protected against hyperpermeability triggered by bacterial toxins.

5. The method of claim 1, wherein the phosphorylation of the myosin light chain is inhibited.

6. The method of claim 1, wherein the peptide is used for inhibiting the activation of protein kinase C.

7. The method of claim 1, wherein the peptide is used for increasing the expression of the epithelial sodium channel.

8. The method of claim 1, wherein the peptide is used for treating hyperpermeability triggered by reactive oxygen molecules, microbial toxins, or pulmonary virus infections.

9. The method of claim 1, wherein the peptide is contained in a pharmaceutical composition comprising the peptide and a pharmaceutical carrier.

10. The method of claim 1, wherein the patient previously had a bacterial or viral lung diseases selected from *Listeria monocytogenes, Streptococcus pneumoniae*, SARS viruses, respiratory syncytial virus (RSV), or influenza viruses.

11. A method of preventing edemas by decreasing hyperpermeability due to damage to endothelial and epithelial layers comprising:
    identifying a patient in need of prevention of edema prior to an onset of lung edema; and
    administering an efficient amount of a peptide with SEQ ID NO. 1 (CGQRETPEGAEAKPWYC) to a patient to prevent lung edemas by decreasing hyperpermeability prior to damage to the endothelial and epithelial layers, wherein the peptide is used for treating hyperpermeability triggered by reactive oxygen molecules, microbial toxins, or pulmonary virus infections.

12. A method of preventing edemas by decreasing hyperpermeability due to damage to endothelial and epithelial layers comprising:
    identifying a patient in need of prevention of edema prior to an onset of lung edema, wherein the patient previously had a bacterial or viral lung diseases selected from *Listeria monocytogenes, Streptococcus pneumoniae*, SARS viruses, RSV or influenza viruses; and
    administering an efficient amount of a peptide with SEQ ID NO. 1 (CGQRETPEGAEAKPWYC) to a patient to prevent lung edemas by decreasing prior to damage to the endothelial and epithelial layers.

13. The method of claim 1, wherein the bacterial or viral lung disease is an infection with *Listeria monocytogenes, Streptococcus pneumoniae*, an influenza virus, a Severe Acute Respiratory Syndrome (SARS) virus, or a respiratory syncytial virus (RSV).

14. The method of claim 1, wherein the patient in need of prevention of edema is a patient with excessive activity of the reactive oxygen molecules- (ROS-) generating NADPH oxidase 2 (NOX2), a patient with sepsis caused by *Streptococcus pneumoniae*, or patients which have undergone lung transplantation.

* * * * *

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial sequence
<220> FEATURE:
<223> OTHER INFORMATION: Synthetic peptide.

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 20
<212> TYPE: PRT
<213> ORGANISM: Artificial sequence
<220> FEATURE:
<223> OTHER INFORMATION: Synthetic peptide.

<400> SEQUENCE: 2

Lys Ser Pro Gly Gly Gln Arg Glu Thr Pro Glu Gly Ala Glu Ala Lys
1               5                   10                  15

Pro Trp Tyr Glu
            20
```

```
<210> SEQ ID NO 3
<211> LENGTH: 17
<212> TYPE: PRT
<213> ORGANISM: Artificial sequence
<220> FEATURE:
<223> OTHER INFORMATION: Synthetic peptide.

<400> SEQUENCE: 3

Cys Gly Gln Arg Glu Ala Pro Ala Gly Ala Ala Ala Lys Pro Trp Tyr
1               5                   10                  15
Cys

<210> SEQ ID NO 4
<211> LENGTH: 6
<212> TYPE: PRT
<213> ORGANISM: Artificial sequence
<220> FEATURE:
<223> OTHER INFORMATION: Synthetic peptide.

<400> SEQUENCE: 4

Thr Pro Glu Gly Ala Glu
1               5

<210> SEQ ID NO 5
<211> LENGTH: 14
<212> TYPE: PRT
<213> ORGANISM: Artificial sequence
<220> FEATURE:
<223> OTHER INFORMATION: Synthetic peptide.

<400> SEQUENCE: 5

Gln Arg Glu Thr Pro Glu Gly Ala Glu Ala Lys Pro Trp Tyr
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic peptide.

<400> SEQUENCE: 6

Pro Lys Asp Thr Pro Glu Gly Ala Glu Leu Lys Pro Trp Tyr
1               5                   10

<210> SEQ ID NO 7
<211> LENGTH: 17
<212> TYPE: PRT
<213> ORGANISM: Artificial sequence
<220> FEATURE:
<223> OTHER INFORMATION: Syntehtic peptide.

<400> SEQUENCE: 7

Cys Gly Pro Lys Asp Thr Pro Glu Gly Ala Glu Leu Lys Pro Trp Tyr
1               5                   10                  15
Cys

<210> SEQ ID NO 8
<211> LENGTH: 17
<212> TYPE: PRT
<213> ORGANISM: Artificial sequence
<220> FEATURE:
<223> OTHER INFORMATION: Synthetic peptide.
```

```
<400> SEQUENCE: 8

Cys Gly Gln Lys Glu Thr Pro Glu Gly Ala Glu Ala Lys Pro Trp Tyr
1               5                   10                  15

Cys

<210> SEQ ID NO 9
<211> LENGTH: 17
<212> TYPE: PRT
<213> ORGANISM: Artificial sequence
<220> FEATURE:
<223> OTHER INFORMATION: Syntehtic peptide.

<400> SEQUENCE: 9

Cys Gly Gln Arg Glu Thr Pro Glu Gly Ala Glu Ala Arg Pro Trp Tyr
1               5                   10                  15

Cys

<210> SEQ ID NO 10
<211> LENGTH: 15
<212> TYPE: PRT
<213> ORGANISM: Artificial sequence
<220> FEATURE:
<223> OTHER INFORMATION: Syntehtic peptide.

<400> SEQUENCE: 10

Cys Gly Gln Arg Glu Thr Pro Glu Gly Ala Glu Ala Lys Pro Cys
1               5                   10                  15

<210> SEQ ID NO 11
<211> LENGTH: 16
<212> TYPE: PRT
<213> ORGANISM: Artificial sequence
<220> FEATURE:
<223> OTHER INFORMATION: Synthetic peptide.

<400> SEQUENCE: 11

Cys Gln Arg Glu Thr Pro Glu Gly Ala Glu Ala Lys Pro Trp Tyr Cys
1               5                   10                  15

<210> SEQ ID NO 12
<211> LENGTH: 17
<212> TYPE: PRT
<213> ORGANISM: Artificial sequence
<220> FEATURE:
<223> OTHER INFORMATION: Synthetic peptide.

<400> SEQUENCE: 12

Cys Gly Gln Arg Glu Thr Pro Glu Gly Ala Glu Ala Lys Phe Trp Tyr
1               5                   10                  15

Cys

<210> SEQ ID NO 13
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
```

```
<400> SEQUENCE: 13

Thr Xaa Glu Xaa Xaa Glu
1               5
```